United States Patent
Coy et al.

(10) Patent No.: US 7,241,737 B2
(45) Date of Patent: Jul. 10, 2007

(54) UROTENSIN-II AGONISTS AND ANTAGONISTS

(75) Inventors: David H. Coy, New Orleans, LA (US); Wojciech J. Rossowski, Kenner, LA (US); John E. Taylor, Upton, MA (US)

(73) Assignees: Societe de Conseils de Recherches et d'Applications Scientifiques, SAS, Paris (FR); The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 10/399,542

(22) PCT Filed: Oct. 19, 2001

(86) PCT No.: PCT/US01/50724

§ 371 (c)(1),
(2), (4) Date: Jul. 19, 2004

(87) PCT Pub. No.: WO02/32932

PCT Pub. Date: Apr. 25, 2002

(65) Prior Publication Data

US 2005/0075480 A1 Apr. 7, 2005

Related U.S. Application Data

(60) Provisional application No. 60/241,896, filed on Oct. 20, 2000.

(51) Int. Cl.
*A61K 38/08* (2006.01)
*C07K 7/06* (2006.01)

(52) U.S. Cl. .......................... 514/11; 514/16; 530/311; 530/328

(58) Field of Classification Search ................. None
See application file for complete search history.

(56) References Cited

U.S. PATENT DOCUMENTS 6,262,229 B1 * 7/2001 Coy et al. .................. 530/311
2002/0107187 A1 * 8/2002 Coy et al. .................... 514/12
2004/0171530 A1 * 9/2004 Coy et al. ..................... 514/9
2004/0181032 A1 * 9/2004 Coy et al. .................. 530/317

FOREIGN PATENT DOCUMENTS

FR 2 786 489 6/2000
WO WO 01/37780 A2 * 5/2001

OTHER PUBLICATIONS

Nishiki, M. et al., "Histopathological Improvement of Acromegalic Cardiomyopathy by Intermittent Subcutaneous Infusion of Octreotide," Endocrine Journal, 1997, 44(5) :655-660.
Newby, D. E. et al., "Urotensin II: Better Than Somatostatin for Portal Hypertension?" Hepatology, 2000, 31(5) : 1201-1202.
Hocart, S. J. et al, "Highly Potent Cyclic Disulfide Antagonists of Somatostatin," J. Medicinal Chem., 1999, 42(11) :1863-1871, XP002189091.
Hocart, S. J. et al. "Potent Antagonists of Somatostatin: Synthesis and Biology," J. Medicinal Chem., 1998, 41:1146-1154, XP000749590.
Waugh, D. et al., "Purification and characterization of urotensin II from the brain of a teleost (trout, *Oncorhynchus mykiss*) and an elasmobranch (skate, *Raja rhina*)," Gen. and Comp. Endo., 1993, 92:419-427.
Coulouarn, Y. et al., "Cloning of the cDNA encoding urotensin II precursor in frog and human reveals intense expression of the urotensin II gene in motoneruons of the spinal cord," PNAS, 1998, 95:15803-15808.

* cited by examiner

*Primary Examiner*—Jeffrey Edwin Russel
(74) *Attorney, Agent, or Firm*—Yankwich & Associates; Alan F. Feeney; Tony K. Uhm

(57) ABSTRACT

The present invention is directed to a novel class of cyclic polypeptides of the formula: $(R^1)_a$-$AA^1$-cyclo[$AA^2$-$AA^3$-$AA^4$-$AA^5$-$AA^6$-Cys]-$AA^7$-$R^2$, pharmaceutically acceptable salts thereof, wherein the variables are as defined in the specification, which inhibit the effects of urotensin-II and are useful for treating a variety of diseases and/or conditions characterized by an excess of urotensin-II including ischaemic heart disease, congestive heart failure, portal hypertension, variceal bleeding, hypotension, angina pectoris, myocardial infarction, ulcers, anxiety, schizophrenia, manic depression, delirium, dementia, mental retardation and/or dyskinesias.

14 Claims, No Drawings

SEQUENCE LISTING

```
<160> NUMBER OF SEQ ID NOS: 13

<210> SEQ ID NO 1
<211> LENGTH: 6
<212> TYPE: PRT
<213> ORGANISM: Artificial Sequence
<220> FEATURE:
<223> OTHER INFORMATION: The cyclic region of U-II

<400> SEQUENCE: 1

Cys Phe Trp Lys Tyr Cys
1               5

<210> SEQ ID NO 2
<211> LENGTH: 4
<212> TYPE: PRT
<213> ORGANISM: Artificial Sequence
<220> FEATURE:
<223> OTHER INFORMATION: Central region of somatostatin-14

<400> SEQUENCE: 2

Phe Trp Lys Thr
1

<210> SEQ ID NO 3
<211> LENGTH: 8
<212> TYPE: PRT
<213> ORGANISM: Artificial Sequence
<220> FEATURE:
<223> OTHER INFORMATION: Minimum portion of the U-II sequence which
      retained full biological activity
<220> FEATURE:
<221> NAME/KEY: MOD_RES
<222> LOCATION: 2, 7
<223> OTHER INFORMATION: Cys at positions 2 and 7 are cyclized
<220> FEATURE:
<221> NAME/KEY: MOD_RES
<222> LOCATION: 8
<223> OTHER INFORMATION: Val-OH
```

```
<400> SEQUENCE: 3

Asp Cys Phe Trp Lys Tyr Cys Val
 1               5

<210> SEQ ID NO 4
<211> LENGTH: 8
<212> TYPE: PRT
<213> ORGANISM: Artificial Sequence
<220> FEATURE:
<223> OTHER INFORMATION: SRIF antagonist
<220> FEATURE:
<221> NAME/KEY: MOD_RES
<222> LOCATION: 2, 7
<223> OTHER INFORMATION: Cys at positions 2 and 7 are cyclized.  Cys at
      position 2 is  a D amino acid.
<220> FEATURE:
<221> NAME/KEY: VARIANT
<222> LOCATION: 1, 8
<223> OTHER INFORMATION: Xaa = Cpa = p-chlorophenylalanine
<220> FEATURE:
<221> NAME/KEY: VARIANT
<222> LOCATION: 3
<223> OTHER INFORMATION: Xaa = Pal = 3-pyridyl-2-alanine
<220> FEATURE:
<221> NAME/KEY: MOD_RES
<222> LOCATION: 4
<223> OTHER INFORMATION: Trp at position 4 is a D amino acid
<220> FEATURE:
<221> NAME/KEY: AMIDATION
<222> LOCATION: 8
<223> OTHER INFORMATION:

<400> SEQUENCE: 4

Xaa Cys Xaa Trp Lys Val Cys Xaa
 1               5

<210> SEQ ID NO 5
<211> LENGTH: 8
<212> TYPE: PRT
<213> ORGANISM: Artificial Sequence
<220> FEATURE:
<223> OTHER INFORMATION: U-II antagonist
<220> FEATURE:
<221> NAME/KEY: MOD_RES
<222> LOCATION: 2, 7
<223> OTHER INFORMATION: Cys at positions 2 and 7 are cyclized.  Cys at
      position 2 is  a D amino acid.
<220> FEATURE:
<221> NAME/KEY: VARIANT
<222> LOCATION: 1
<223> OTHER INFORMATION: Xaa = Cpa = p-chlorophenylalanine
<220> FEATURE:
<221> NAME/KEY: AMIDATION
<222> LOCATION: 8
<223> OTHER INFORMATION:

<400> SEQUENCE: 5

Xaa Cys Phe Trp Lys Thr Cys Val
 1               5

<210> SEQ ID NO 6
<211> LENGTH: 8
<212> TYPE: PRT
<213> ORGANISM: Artificial Sequence
<220> FEATURE:
<223> OTHER INFORMATION: SRIF Antagonist
<220> FEATURE:
<221> NAME/KEY: VARIANT
<222> LOCATION: 1
<223> OTHER INFORMATION: Xaa = Nal
<220> FEATURE:
<221> NAME/KEY: MOD_RES
```

```
<222> LOCATION: 2
<223> OTHER INFORMATION: Cys at position 2 is a D amino acid.
<220> FEATURE:
<221> NAME/KEY: MOD_RES
<222> LOCATION: 4
<223> OTHER INFORMATION: Trp at position 4 is a D amino acid.
<220> FEATURE:
<221> NAME/KEY: VARIANT
<222> LOCATION: 8
<223> OTHER INFORMATION: Xaa =D-Dip=D-2,2-diphenylalanine
<220> FEATURE:
<221> NAME/KEY: AMIDATION
<222> LOCATION: 8
<223> OTHER INFORMATION:

<400> SEQUENCE: 6

Xaa Cys His Trp Lys Val Cys Xaa
 1               5

<210> SEQ ID NO 7
<211> LENGTH: 8
<212> TYPE: PRT
<213> ORGANISM: Artificial Sequence
<220> FEATURE:
<223> OTHER INFORMATION: SRIF Antagonist
<220> FEATURE:
<221> NAME/KEY: VARIANT
<222> LOCATION: 1
<223> OTHER INFORMATION: Xaa = 4Fpa
<220> FEATURE:
<221> NAME/KEY: MOD_RES
<222> LOCATION: 2
<223> OTHER INFORMATION: Cys at position 2 is a D amino acid
<220> FEATURE:
<221> NAME/KEY: VARIANT
<222> LOCATION: 3
<223> OTHER INFORMATION: Xaa = Pal = 3-pyridyl-2-alanine
<220> FEATURE:
<221> NAME/KEY: MOD_RES
<222> LOCATION: 4
<223> OTHER INFORMATION: D-Trp
<220> FEATURE:
<221> NAME/KEY: AMIDATION
<222> LOCATION: 8
<223> OTHER INFORMATION:
<220> FEATURE:
<221> NAME/KEY: VARIANT
<222> LOCATION: (8)...(8)
<223> OTHER INFORMATION: Xaa = Nal = 3-(2-naphthyl)-alanine or
     3-(1-naphthyl)-alanine

<400> SEQUENCE: 7

Xaa Cys Xaa Xaa Lys Val Cys Xaa
 1               5

<210> SEQ ID NO 8
<211> LENGTH: 8
<212> TYPE: PRT
<213> ORGANISM: Artificial Sequence
<220> FEATURE:
<223> OTHER INFORMATION: SRIF Antagonist
<220> FEATURE:
<221> NAME/KEY: VARIANT
<222> LOCATION: 1
<223> OTHER INFORMATION: Xaa = 4Fpa
<220> FEATURE:
<221> NAME/KEY: MOD_RES
<222> LOCATION: 2
<223> OTHER INFORMATION: Cys at position 2 is  a D amino acid.
<220> FEATURE:
<221> NAME/KEY: VARIANT
<222> LOCATION: 3
<223> OTHER INFORMATION: Xaa = Pal = 3-pyridyl-2-alanine
<220> FEATURE:
<221> NAME/KEY: MOD_RES
```

```
<222> LOCATION: 4
<223> OTHER INFORMATION: D-Trp
<220> FEATURE:
<221> NAME/KEY: VARIANT
<222> LOCATION: 6
<223> OTHER INFORMATION: Xaa = Tle = tert-leucine
<220> FEATURE:
<221> NAME/KEY: VARIANT
<222> LOCATION: (8)...(8)
<223> OTHER INFORMATION: Xaa = Nal= 3-(2-naphthyl)-alanine or
      3-(1-naphthyl)-alanine
<220> FEATURE:
<221> NAME/KEY: AMIDATION
<222> LOCATION: (8)...(8)
<223> OTHER INFORMATION:

<400> SEQUENCE: 8

Xaa Cys Xaa Trp Cys Xaa Cys Xaa
 1               5

<210> SEQ ID NO 9
<211> LENGTH: 8
<212> TYPE: PRT
<213> ORGANISM: Artificial Sequence
<220> FEATURE:
<223> OTHER INFORMATION: SRIF Antagonist
<220> FEATURE:
<221> NAME/KEY: VARIANT
<222> LOCATION: 1
<223> OTHER INFORMATION: Xaa = Cpa = p- chlorophenylanaline
<220> FEATURE:
<221> NAME/KEY: MOD_RES
<222> LOCATION: 2
<223> OTHER INFORMATION: Cys at position 2 is  a D amino acid.
<220> FEATURE:
<221> NAME/KEY: MOD_RES
<222> LOCATION: 4
<223> OTHER INFORMATION: Trp at position 4 is a D amino acid
<220> FEATURE:
<221> NAME/KEY: AMIDATION
<222> LOCATION: 8
<223> OTHER INFORMATION:
<220> FEATURE:
<221> NAME/KEY: VARIANT
<222> LOCATION: 8
<223> OTHER INFORMATION: Xaa = Nal = 3-(2-naphthyl)-alanine or
      3-(1-naphthyl-alanine

<400> SEQUENCE: 9

Xaa Cys Tyr Trp Lys Thr Cys Xaa
 1               5

<210> SEQ ID NO 10
<211> LENGTH: 8
<212> TYPE: PRT
<213> ORGANISM: Artificial Sequence
<220> FEATURE:
<223> OTHER INFORMATION: Antagonist
<220> FEATURE:
<221> NAME/KEY: VARIANT
<222> LOCATION: 1
<223> OTHER INFORMATION: Xaa = Cpa
<220> FEATURE:
<221> NAME/KEY: MOD_RES
<222> LOCATION: 2
<223> OTHER INFORMATION: Cys at position 2 is D-Cys
<220> FEATURE:
<221> NAME/KEY: VARIANT
<222> LOCATION: 3
<223> OTHER INFORMATION: Xaa = Pal
<220> FEATURE:
<221> NAME/KEY: MOD_RES
<222> LOCATION: 4
<223> OTHER INFORMATION: Trp at position 4 is D-Trp
<220> FEATURE:
```

```
<221> NAME/KEY: VARIANT
<222> LOCATION: 6
<223> OTHER INFORMATION: Xaa = Tle = tert-leucine
<220> FEATURE:
<221> NAME/KEY: VARIANT
<222> LOCATION: (8)...(8)
<223> OTHER INFORMATION: Xaa = Nal = 3-(2-naphthyl)-alanine or
      3-(1-naphthyl)-alanine
<220> FEATURE:
<221> NAME/KEY: AMIDATION
<222> LOCATION: (8)...(8)
<223> OTHER INFORMATION:

<400> SEQUENCE: 10

Xaa Cys Xaa Trp Lys Xaa Cys Xaa
 1               5

<210> SEQ ID NO 11
<211> LENGTH: 8
<212> TYPE: PRT
<213> ORGANISM: Artificial Sequence
<220> FEATURE:
<223> OTHER INFORMATION: SRIF Antagonist
<220> FEATURE:
<221> NAME/KEY: VARIANT
<222> LOCATION: 1, 8
<223> OTHER INFORMATION: Xaa = Cpa
<220> FEATURE:
<221> NAME/KEY: MOD_RES
<222> LOCATION: 2
<223> OTHER INFORMATION: Cys at position 2 is a D amino acid.
<220> FEATURE:
<221> NAME/KEY: VARIANT
<222> LOCATION: 3
<223> OTHER INFORMATION: Pal
<220> FEATURE:
<221> NAME/KEY: AMIDATION
<222> LOCATION: 8

<400> SEQUENCE: 11

Xaa Cys Xaa Trp Lys Thr Cys Xaa
 1               5

<210> SEQ ID NO 12
<211> LENGTH: 8
<212> TYPE: PRT
<213> ORGANISM: Artificial Sequence
<220> FEATURE:
<223> OTHER INFORMATION: General formula for class of cyclic
      polypeptides that have U-II antagonist activity
<220> FEATURE:
<221> NAME/KEY: VARIANT
<222> LOCATION: 1
<223> OTHER INFORMATION: Xaa = L isomer of an aromatic amino acid.
<220> FEATURE:
<221> NAME/KEY: MOD_RES
<222> LOCATION: 1
<223> OTHER INFORMATION: Xaa may be modified with one or two of H, a
      lower alkyl, lower alkanoyl, or a lower acyl.
<220> FEATURE:
<221> NAME/KEY: DOMAIN
<222> LOCATION: (1)...(8)
<223> OTHER INFORMATION: The peptide is not
      Cpa-c <220> FEATURE:
<221> NAME/KEY: VARIANT
<222> LOCATION: 2
<223> OTHER INFORMATION: Xaa= the L or D isomer of Cys
<220> FEATURE:
<221> NAME/KEY: DOMAIN
<222> LOCATION: (2)...(7)
<223> OTHER INFORMATION: Cyclic
<220> FEATURE:
<221> NAME/KEY: VARIANT
```

```
<222> LOCATION: (3)...(3)
<223> OTHER INFORMATION: Xaa = the L isomer of an aromatic amino acid
<220> FEATURE:
<221> NAME/KEY: VARIANT
<222> LOCATION: (4)...(4)
<223> OTHER INFORMATION: Xaa = the L or D isomer of Trp
<220> FEATURE:
<221> NAME/KEY: VARIANT
<222> LOCATION: (5)...(5)
<223> OTHER INFORMATION: Xaa = the L or D isomer of Lys, N-Me-Lys, or
      Orn
<220> FEATURE:
<221> NAME/KEY: VARIANT
<222> LOCATION: (6)...(6)
<223> OTHER INFORMATION: Xaa = the L or D isomer of Val, Thr, Leu, Ile,
      tert-Leu, Abu, Nle, or an aromatic amino acid
<220> FEATURE:
<221> NAME/KEY: VARIANT
<222> LOCATION: (8)...(8)
<223> OTHER INFORMATION: Xaa = the L or D isomer of Val, Thr, Leu, Ile,
      tert-Leu, Abu, Nle, or an aromatic amino acid
<220> FEATURE:
<221> NAME/KEY: MOD_RES
<222> LOCATION: (8)...(8)
<223> OTHER INFORMATION: Xaa may be modified by OH, OR3, N (R3) 2, or
      NHR3, where R3 is H, a lower alkyl or arylalkyl

<400> SEQUENCE: 12

Xaa Xaa Xaa Xaa Xaa Xaa Cys Xaa
 1               5

<210> SEQ ID NO 13
<211> LENGTH: 8
<212> TYPE: PRT
<213> ORGANISM: Artificial Sequence
<220> FEATURE:
<223> OTHER INFORMATION: Provided formula peptide is not this peptide
<220> FEATURE:
<221> NAME/KEY: VARIANT
<222> LOCATION: 1
<223> OTHER INFORMATION: Xaa = Cpa = p-chlorophenylalanine
<220> FEATURE:
<221> NAME/KEY: VARIANT
<222> LOCATION: 2
<223> OTHER INFORMATION: Xaa = D-Cys
<220> FEATURE:
<221> NAME/KEY: DOMAIN
<222> LOCATION: (2)...(7)
<223> OTHER INFORMATION: Cyclic
<220> FEATURE:
<221> NAME/KEY: VARIANT
<222> LOCATION: 3
<223> OTHER INFORMATION: Xaa = Pal = 3-pyridyl-2-alanine
<220> FEATURE:
<221> NAME/KEY: VARIANT
<222> LOCATION: 4
<223> OTHER INFORMATION: Xaa = D-Trp
<220> FEATURE:
<221> NAME/KEY: VARIANT
<222> LOCATION: (8)...(8)
<223> OTHER INFORMATION: Xaa = Cpa = p=chlorophenylalanine
<220> FEATURE:
<221> NAME/KEY: MOD_RES
<222> LOCATION: (8)...(8)
<223> OTHER INFORMATION: Amidation

<400> SEQUENCE: 13

Xaa Xaa Xaa Xaa Lys Val Cys Xaa
 1               5
```

US 7,241,737 B2

UROTENSIN-II AGONISTS AND ANTAGONISTS

CROSS-REFERENCE TO RELATED APPLICATIONS

This application is the National Stage of International Application No. PCT/US01/50724, filed Oct. 19, 2001, which was published in English under PCT Article 21(2). This application also claims benefit of U.S. Provisional Application No. 60/241,896, filed Oct. 20, 2000.

FIELD OF THE INVENTION

The invention relates to urotensin-II polypeptide agonists and antagonists and methods of their use.

BACKGROUND OF THE INVENTION

Urotensin-II (U-II) is a cyclic neuropeptide with potent cardiovascular effects. Originally isolated from the caudal neurosecretory system of teleost fish, the primary structure of U-II has been established for several species of vertebrates, including various fish species, frogs, and humans. Sequence analysis of various U-II peptides from different species has revealed that, while the N-terminal region is highly variable, the C-terminal cyclic region of U-II is strongly conserved. Indeed, this cyclic region, which is responsible for the biological activity of U-II, is fully conserved from fish to humans (Coulouran, et al., *Proc. Natl. Acad. Sci. USA* (physiology), 95:15803-15808 (1998)). The fact that evolutionary pressure has acted to fully conserve the biologically active sequence of U-II suggests that this polypeptide plays an important role in human physiology.

The cyclic region of U-U includes six amino acid residues (-Cys-Phe-Trp-Lys-Tyr-Cys-(SEQ ID NO: 1)) and is structurally similar to the biologically important central region of somatostatin-14 (-Phe-Trp-Lys-Thr-(SEQ ID NO: 2)). However, molecular cloning and sequence analysis of the carp preprourotensin II gene suggests that U-II and somatostatin are not derived from a common ancestor (Ohsako, S., et al., *J. Neurosci.*, 6:2730-2735 (1986)).

In fish, U-II peptides have been shown to exhibit several activities, including general smooth muscle contracting activity, although responses vary between species and vascular beds (Davenport, A., and Maquire, J., *Trends in Pharmacological Sciences*, 21:80-82 (2000); Bern, H. A., et al., *Recent Prog. Horm. Res.*, 45:533-552 (1995)). Fish U-II has also been shown to possess constrictor activity in mammals, including major arteries in rats, but the receptor(s) mediating these peptide actions are not fully characterized.

Recent studies have reported that an orphan human G-protein-coupled receptor, homologous to the rat GPR14 and expressed predominantly in cardiovascular tissue, functions as an U-II receptor (Ames, H., et al., *Nature*, 401:282-286 (1999)). Fish (goby) and human U-II reportedly bind to recombinant human GPR14 with high affinity, and the binding is functionally coupled to calcium mobilization. Human U-II is found within both vascular and cardiac tissue (including coronary atheroma) and effectively constricts isolated arteries from non-human primates (Ames, H., et al., supra). The potency of vasoconstriction of U-II is substantially greater than that of endothelin-1, making human U-II one of most potent mammalian vasoconstrictors currently known. In vivo, human U-II markedly increases total peripheral resistance in anaesthetized non-human primates, a response associated with profound cardiac contractile dysfunction (Ames, H., et al., supra).

Since human U-II-like immunoreactivity is found within cardiac and vascular tissue (including coronary atheroma), U-II is believed to influence cardiovascular homeostasis and pathology (e.g., ischemic heart disease and congestive heart failure). Furthermore, the detection of U-II immunoreactivity within spinal cord and endocrine tissues suggests that U-II may have additional activities, including modulation of central nervous system and endocrine function in humans (Ames, H., et al., supra). Indeed, a number of maladies have been potentially linked to an excess or an under expression of U-II activity, including ischemic heart failure, hypotension, portal hypertension, angina pectoris, variceal bleeding, myocardial infarction, ulcers, and certain psychological and neurological disorders. Thus, there is a strong need for the development of potent compounds capable of modulating U-II activity, including U-II inhibitors or antagonists.

SUMMARY OF THE INVENTION

The present invention features a novel class of cyclic polypeptides that have U-II antagonist activity. The polypeptides of the invention are octapeptides having the general formula: $(R^1)_a$-$AA^1$-cyclo[$AA^2$-$AA^3$-$AA^4$-$AA^5$-$AA^6$-Cys]-$AA^7$-$R^2$ (Formula I), wherein $AA^1$ is the L isomer of an aromatic amino acid; $AA^2$ is the L or D isomer of Cys; $AA^3$ is an L isomer of an aromatic amino acid; $AA^4$ is the L or D isomer of Trp; $AA^5$ is the L or D isomer of Lys, N-Me-Lys, or Orn; $AA^6$ is the L or D isomer of Val, Thr, Leu, Ile, tert-Leu, Abu, Nle, or an aromatic amino acid; $AA^7$ is the L or D isomer of Val, Thr, Leu, Ile, tert-Leu, Abu, Nle, or an aromatic amino acid; $R^1$ is H, a lower alkyl, lower alkanoyl, or a lower acyl; a is 1 or 2; and $R^2$ is OH, $OR^3$, $N(R^3)_2$, or $NHR^3$, where $R^3$ is H, a lower alkyl, or arylalkyl; provided that the peptide is not Cpa-c[D-Cys-Pal-D-Trp-Lys-Val-Cys]-Cpa-$NH_2$.

In a preferred embodiment, $AA^2$ and $AA^4$ are D-Cys and L-Trp, respectively.

In another preferred polypeptide, $AA^1$ is Cpa, $AA^2$ is D-Cys, $AA^3$ is Phe, $AA^4$ is Trp, $AA^5$ is Lys, $AA^6$ is Thr, and $AA^7$ is Val.

In a particularly preferred embodiment, the polypeptide is an octapeptide having the formula Cpa-c[D-Cys-Phe-Trp-Lys-Thr-Cys]-Val-$NH_2$.

The invention also provides a Urotensin-II agonist polypeptide, and variants thereof, having the formula Asp-c[Cys-Phe-Trp-Lys-Tyr-Cys]-Val-OH.

The polypeptides of the present invention are capable of altering U-II activity and can affect the binding of U-II to a receptor. Thus, these polypeptides may be administered to a subject as a means for preventing or treating medical or psychological conditions characterized by an excess or deficiency or under expression of Urotensin-It activity. Such conditions include, but are not limited to, ischaemic heart disease, congestive heart failure, portal hypertension, variceal bleeding, hypotension, angina pectoris, myocardial infarction, ulcers, anxiety, schizophrenia, manic depression, delirium, dementia, mental retardation, and dyskinesias.

The present invention also provides pharmaceutical compositions that include a therapeutically effective amount of a polypeptide of Formula I in combination with a pharmaceutically acceptable carrier. Suitable carriers include, but are not limited to, saline, buffered saline, dextrose, water, glycerol, ethanol, and combinations thereof. The composition can be adapted for the mode of administration and can be in the form of a pill, tablet, capsule, spray, powder, or liquid.

Other features and advantages of the invention will be apparent from the following detailed description thereof, and from the claims.

DEFINITIONS

By "polypeptide" is meant any peptide (including cyclic peptides) or protein comprising two or more amino acids joined to each other by peptide bonds or modified peptide bonds. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, or by chemical modification techniques which are well known in the art. Modifications may occur anywhere in a polypeptide, including the peptide backbone, the amino acid side-chains, and the amino or carboxyl termini.

The notations used herein for the polypeptide amino acid residues are those abbreviations commonly used in the art. The less common abbreviations Abu, Cpa, Nle, Pal, Tle, Dip, 4-Fpa, and Nal stand for 2-amino-butyric acid, p-chloroPhenylalanine, norleucine, 3-pyridyl-2-alanine, tert-leucine, 2,2-diphenylalanine, 4-fluoro-phenylalanine, and 3-(2-naphthyl)-alanine or 3-(1-naphthyl)-alanine, respectively.

By "alkyl" is meant an aliphatic branched or straight chain hydrocarbon group. An alkyl is optionally substituted with one or more substituents, which may be the same or different, selected from the group consisting of halo, cycloalkyl, hydroxy, alkoxy, amino, carbamoyl, acylamino, aroylamino, carboxy, alkoxycarbonyl, aralkyloxycarbonyl and heteroaralkyloxycarbonyl groups. Alkyl groups, that may be incorporated into the claimed urotensin-II polypeptides antagonists are selected from the group consisting of methyl, trifluoromethyl, cyclopropylmethyl, cyclopentylmethyl, ethyl, n-propyl, i-propyl, n-butyl, t-butyl, n-pentyl, 3-pentyl, methoxyethyl and carboxymethyl. By "lower alkyl" is meant a branched or straight chain alkyl group having less than 11 carbon atoms, preferably a ($C_1$-$C_8$) alkyl.

By "acyl" is meant a group having the structure

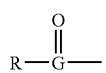

wherein R is H or an alkyl group as described herein. By "lower acyl" is meant an acyl group having less than 11 carbon atoms (either branched or straight chain), preferably between 1-8 carbon atoms (i.e., R is H or a lower alkyl).

By "lower alkanoyl" is meant an acyl group as described above wherein R is a lower alkyl.

By "aryl" is meant a monocyclic or bicyclic aromatic group containing from 6 to 12 carbons in the ring portion, preferably 6-10 carbons in the ring portion, such as phenyl, napthyl or tetrahydronaphthyl. By "arylalkyl" is meant an alkyl group as described herein having an aryl substituent, such as benzyl, phenylethyl or 2-naphthylmethyl.

By "pharmaceutically acceptable salt" is meant non-toxic acid addition salts or metal complexes which are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like.

By "subject" is meant an animal or human suffering from a U-II-related physiological or psychological condition. The subject may be a mammal, including, but not limited to, humans and non-human mammals such as primates, dogs, cats, pigs, cows, sheep, goats, horses, rats, mice, and the like.

By "pharmaceutically acceptable carrier" is meant a carrier that is physiologically acceptable to an administered animal while retaining the therapeutic properties of the compound with which it is administered. One exemplary pharmaceutically acceptable carrier is physiological saline. Other physiologically acceptable carriers and their formulations are known to one skilled in the art and described, for example, in *Remington's Pharmaceutical Sciences*, (18th edition), ed. A. Gennaro, 1990, Mack Publishing Company, Easton, Pa.

By "aromatic amino acid" is meant an amino acid that contains an aromatic group.

In preferred embodiments, the aromatic amino acid has the following formula:

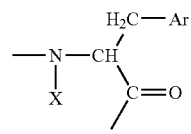

(Formula II), where Ar is a moiety containing an optionally substituted aromatic ring.

Examples of Ar, include but are not limited to, the following structures wherein $Y_{11}$ represents n optional substituents and n is 0, 1, 2, or 3:

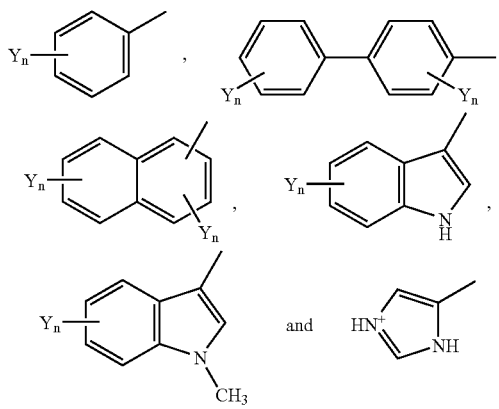

In preferred embodiments, each substituent Y independently represents $NO_2$, CN, Cl, Br, I, F, Me, $COR^4$, $COOR^4$, or $OR^4$, groups, where $R^4$ is H or $C_1$-$C_8$ alkyl. Examples of aromatic amino acids include, but are not limited to, Phe, Cpa, Trp, Pal, His, β-Nal, 3-pyridyl-Ala, 4-pyridyl-Ala, 2,4-dichloro-phe, pentafluoro-Phe, p-Z-Phe, and o-Z-Phe, wherein Z is selected from the group consisting of Me, Cl, Br, F, OH, OMe, and $NO_2$.

DETAILED DESCRIPTION

We found that the minimum portion of the U-II sequence which retained full biological activity was the octapeptide Asp-c[Cys-Phe-Trp-Lys-Tyr-Cys]-Val-OH (SEQ ID NO: 3), which corresponds to hUII(4-7). This octapeptide actually possess greater potency than the full human and fish U-II sequences in inducing rat aorta contraction and in binding to this tissue.

Based on this parent sequence, a series of cyclic octapeptides have been synthesized which have U-II antagonist activity. These peptides were discovered to have moderate affinity for U-II receptors and were able to block U-II-induced phasic contracts in circular rat thoracic aorta strips. The polypeptides of the present invention have the general formula: $(R^1)_a$-AA$^1$-cyclo[AA$^2$-AA$^3$-AA$^4$-AA$^5$-AA$^6$-Cys]-AA$^7$-R$^2$ (Formula I), wherein AA$^1$ is the L isomer of an aromatic amino acid; AA$^2$ is the L or D isomer of Cys; AA$^3$ is an L isomer of an aromatic amino acid; AA$^4$ is the L or D isomer of Trp; AA$^5$ is the L or D isomer of Lys, N-Me-Lys, or Orn; AA$^6$ is the L or D isomer of Val, Thr, Leu, Ile, tert-Leu, Abu, Nle, or an aromatic amino acid; AA$^7$ is the L or D isomer of Val, Thr, Leu, Ile, tert-Leu, Abu, Nle, or an aromatic amino acid; R$^1$ is H, a lower alkyl, lower alkanoyl, or a lower acyl; a is 1 or 2; and R$^2$ is OH, OR$^3$, N(R$^3$)$_2$, or NHR$^3$, where R$^3$ is H, a lower alkyl, or arylalkyl.

One of the most potent U-II inhibitors tested was the SRIF antagonist Cpa-c[D-Cys-Pal-D-Trp-Lys-Val-Cys]-Cpa-amide (SEQ ID NO: 4), which had an IC$_{50}$ of about 100 nM and Kd of 240. Another potent U-II antagonist was Cpa-c[D-Cys-Phe-Trp-Lys-Thr-Cys]-Val-NH$_2$ (SEQ ID NO: 5) which had an IC$_{50}$ of about 2 nM. Other SRIF antagonists that were tested are summarized in Example 2 below (see table 1).

The polypeptides of the invention are capable of modulating U-II activity and are, therefore, useful for treating physiological and psychological conditions related to either an excess of or an under expression of U-II activity within a subject. Such conditions include, for example, acute heart failure, hypotension, hypertension, angina pectoris, variceal bleeding, myocardial infarction, ulcers, and certain psychological and neurological disorders, including anxiety, schizophrenia, manic depression, delirium, dementia, mental retardation and dyskinesias.

If the condition stems from an excess of U-II activity, one approach to treatment is to administer to a subject in need thereof an inhibitor compound (antagonist), optionally in combination with a pharmaceutically acceptable carrier, in an amount effective to inhibit the function of U-II. Alternatively, for treating conditions related to under expression of U-II activity, a compound which activates U-II (agonist) is administered.

A therapeutically effective amount of a polypeptide of Formula I, or a variant or pharmaceutically acceptable salt-thereof, can be administered orally, parenterally (e.g. intramuscular, intraperitoneal, intravenous or subcutaneous injection, or implant), nasally, vaginally, rectally, sublingually or topically, in admixture with a pharmaceutically acceptable carrier adapted for the route of administration.

Methods well known in the art for making formulations are found, for example, in *Remington's Pharmaceutical Sciences* (18$^{th}$ edition), ed. A. Gennaro, 1990, Mack Publishing Company, Easton, Pa. Compositions intended for oral use may be prepared in solid or liquid forms according to any method known to the art for the manufacture of pharmaceutical compositions. The compositions may optionally contain sweetening, flavoring, coloring, perfuming, and/or preserving agents in order to provide a more palatable preparation. Solid dosage forms for oral administration include capsules, tablets, pills, powders, and granules. In such solid forms, the active compound is admixed with at least one inert pharmaceutically acceptable carrier or excipient. These may include, for example, inert diluents, such as calcium carbonate, sodium carbonate, lactose, sucrose, starch, calcium phosphate, sodium phosphate, or kaolin. Binding agents, buffering agents, and/or lubricating agents (e.g., magnesium stearate) may also be used. Tablets and pills can additionally be prepared with enteric coatings.

Liquid dosage forms for oral administration include pharmaceutically acceptable emulsions, solutions, suspensions, syrups, and soft gelatin capsules. These forms contain inert diluents commonly used in the art, such as water or an oil medium. Besides such inert diluents, compositions can also include adjuvants, such as wetting agents, emulsifying agents, and suspending agents.

Formulations for parenteral administration include sterile aqueous or non-aqueous solutions, suspensions, or emulsions. Examples of suitable vehicles include propylene glycol, polyethylene glycol, vegetable oils, gelatin, hydrogenated naphalenes, and injectable organic esters, such as ethyl oleate. Such formulations may also contain adjuvants, such as preserving, wetting, emulsifying, and dispersing agents. Biocompatible, biodegradable lactide polymer, lactide/glycolide copolymer, or polyoxyethylene-polyoxypropylene copolymers may be used to control the release of the compounds. Other potentially useful parenteral delivery systems for the polypeptides of the invention include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, they can also be manufactured in the form of sterile, solid compositions which can be dissolved in sterile water or some other sterile injectable medium immediately before use.

Compositions for rectal or vaginal administration are preferably suppositories which may contain, in addition to active substances, excipients such as coca butter or a suppository wax. Compositions for nasal or sublingual administration are also prepared with standard excipients known in the art. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops or spray, or as a gel.

The amount of active ingredient in the compositions of the invention can be varied. One skilled in the art will appreciate that the exact individual dosages may be adjusted somewhat depending upon a variety of factors, including the polypeptide being administered, the time of administration, the route of administration, the nature of the formulation, the rate of excretion, the nature of the subject's conditions, and the age, weight, health, and gender of the patient. In addition, the severity of the U-II-related condition being treated will also have an impact on the dosage level. Generally, dosage levels of between 0.1 µg/kg to 100 mg/kg of body weight are administered daily as a single dose or divided into multiple doses. Preferably, the general dosage range is between 250 µg/kg to 5.0 mg/kg of body weight per day. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise therapeutically effective dosage will be determined by the attending physician in consideration of the above identified factors.

The polypeptides of the invention can be administered in a sustained release composition, such as those described in, for example, U.S. Pat. Nos. 5,672,659 and 5,595,760. The use of immediate or sustained release compositions depends on the type of condition being treated. If the condition consists of an acute or over-acute disorder, a treatment with an immediate release form will be preferred over a prolonged release composition. Alternatively, for preventative or long-term treatments, a sustained released composition will generally be preferred.

Polypeptides of the present invention can be prepared in any suitable manner. The polypeptides may be isolated from naturally occurring sources, recombinantly produced, or produced synthetically, or produced by a combination of these methods. The synthesis of short peptides is well known in the art. See e.g. Stewart et al., Solid Phase Peptide Synthesis (Pierce Chemical Co., 2d ed., 1984). The peptides of the present invention can be synthesized according to standard peptide synthesis methods known in the art and exemplified in Example 1 below.

The present invention is illustrated by the following examples, which are in no way intended to be limiting of the invention.

EXAMPLE 1

Preparation of
Cpa-c[D-Cys-Pal-D-Trp-Lys-Val-Cys]-Cpa-amide

Step 1: Preparation of Boc-4-chlorophenylalanine-S-methylbenzyl-D-cysteine-3-pyridyl-2-alanine-D-tryptophan-$N^\alpha$-benzyloxycarbonyl-lysine-valine-S-methylbenzyl-cysteine-4-chlorophenylalanine-benzhydrylamine resin Benzhydrylamine-polystyrene resin (Advanced ChemTech, Inc., Louisville, Ky.) (1.2 g, 0.5 mmole) in the chloride ion form was placed in the reaction vessel of an Advanced ChemTech peptide synthesizer (Model 200) programmed to perform the following reaction cycle: (a) methylene chloride; (b) 33% trifluoroacetic acid in methylene chloride (2 times for 1 min. and 25 min. each); (c) methylene chloride; (d) ethanol; (e) methylene chloride; (f) 10% triethylamine in chloroform.

The neutralized resin is stirred with Boc-4-chlorophenylalanine and diisopropylcarbodiimide (1.5 mmole each) in methylene chloride for 1 hour and the resulting amino acid resin in then cycled through steps (a) through (f) in the above wash program. The following amino acids (1.5 mmole) are then coupled successively by the same procedure: Boc-S-methylbenzyl-Cys, Boc-Val, Boc-$N^\alpha$-benzyloxycarbonyl-lysine, Boc-D-Trp, Boc-Pal, and Boc-S-methylbenzyl-D-Cys and Boc-4-chlorophenylalanine. After washing and drying, the completed resin weighed about 2.0 g.

Step 2: Deprotection and Cleavage from Resin

The resin described in Step 1 (1.0 g, 0.25 mmole) was mixed with anisole (5 ml), dithiothretol (100 mg), and anhydrous hydrogen fluoride (35 ml) at about 0° C. and stirred for 45 min. Excess hydrogen fluoride was evaporated rapidly under a stream of dry nitrogen, after which free peptide was precipitated and washed with ether. The crude peptide was then dissolved in 500 ml of 90% acetic acid. A concentrated solution of $I_2$/MeOH was then added until a permanent brown color was observed. Excess $I_2$ was removed by the addition of ascorbic acid and the solution evaporated to a small volume which was applied to a column (2.5×90 cm) of VYDAC™ octadecylsilane silica (10-15 µm). This was eluted with a linear gradient of acetonitrile in 0.1% trifluoroacetic acid in water. Fractions were examined by thin layer chromatography and analytic high performance liquid chromatography and pooled to give maximum purity. Repeated lyophilization of the solution from water gave 125 mg of the desired product as a white, fluffy powder.

The product was found to be homogenous by HPLC and TLC. Amino acid analysis of an acid hydrolysate and matrix-assisted laser desorption MS confirmed the composition of the octapeptide. Other peptide of the invention may be made using an analogous procedure with appropriate reactants.

EXAMPLE 2

Use of Rat Aorta Circular Strip for Assay U-II Antagonists

Male Sprague-Dawley rats (250-350 g), which had been quarantined for 5-7 days prior to the experiments, were sacrificed by decapitation (experiments were approved by the Advisory Committee For Animal Resources, Tulane University School of Medicine). The thoracic aorta was dissected, freed from connective tissue, and cut into rings of about 1.5 mm in width. The rings were suspended in a 15 ml organ bath containing high potassium Kreb's solution (9.15 g/L potassium chloride, 2.1 g/L sodium bicarbonate, 1.0 g/L glucose, 0.16 g/L potassium phosphate monobasic, 0.14 g/L magnesium sulfate (anhydr.), and 0.22 g/L calcium chloride (dihydr.))

Optimal tension was applied (0.2 g) to the tissues and the bath medium was maintained at 37° C. and bubbled with a mixture of 95% $O_2$/5% $CO_2$. Prior to mounting in the organ bath, selected preparations were rubbed with a moistened cotton wool swab, in order to remove the endothelial cell layer, and the effect of this procedure was tested using an acetylcholine-relaxation test. (Gibson, A., Br. J. Pharmacol. 91:205 (1987)). The aorta rings were allowed to equilibrate for 90 min. at the optimal tensions. During the equilibration period, the bath solution was replaced every 15 min. Contractile responses of aortae rings to various concentrations of peptides were expressed in volts. Changes in arterial smooth muscle tension were recorded isometrically using a force-displacement transducer (Radnoti), and a AcqKnowledge ACK100 Version 3.2 (BIOPAC Systems, Inc., Santa Barbara, Calif.)

In siliconized glass tubes, peptides were dissolved in dionized water at a concentration of 1 µg/1 µL (stock solution) and then diluted 1:10 with sterile BSA-saline solution (0.1% BSA, fraction V, Sigma, St. Louis in 0.9% NaCl). All peptide solutions were prepared fresh directly before the experiments. Peptides in the concentration ranges of $10^{-6}$ to $10^{-12}$ M/L in a final volume of 16-80 µL were direcly introduced into the tested organ bath containing Krebs buffer continuously gassed with 95% $O_2$ and 5% $CO_1$, and the aorta rings at an optimal resting tension (1-0.2 g). Peptide-induced changes in tension of the aorta rings were recorded by force-displacement transducers and processed by the computer system BIOPAC Inc., as described above. Each ring was exposed to one peptide concentration only.

Using assay techniques known in the art, we found that the minimally, fully potent sequence of U-II was the octapeptide Asp-c[Cys-Phe-Trp-Lys-Tyr-Cys]-Val-OH (SEQ ID NO: 3), which was actually more potent than the full human and fish sequences in inducing rat aorta contracts. Various somatostatin (SRIF) antagonists were discovered to have the ability to block UII-induced phase contractions in the circular rat thoracic aorta strips. One of the most potent inhibitors was the SRIF antagonist Cpa-c[D-Cys-Pal-D-Trp-Lys-Val-Cys]-Cpa-amide (SEQ ID NO: 4), which had an $IC_{50}$ of about 100 nM and a Kd of 240 nM. The polypeptide Cpa-c[D-Cys-Phe-Trp-Lys-Thr-Cys]-ValNH$_2$ was also a strong U-II antagonist with an $IC_{50}$ of 2 nM. Other compounds that were tested are summarized in Table 1 below.

TABLE 1

SRIF Antagonist IC$_{50}$s (nM) against U-II Stimulation of Rat Aorta Phasic Contractions

| Polypeptide | | IC$_{50}$ |
|---|---|---|
| Nal-D-Cys-His-D-Trp-Lys-Val-Cys-D-Dip-NH$_2$ | (SEQ ID NO: 6) | 1800 |
| 4Fpa-D-Cys-Pal-D-Trp-Lys-Val-Cys-Nal-NH$_2$ | (SEQ ID NO: 7) | 1090 |
| 4Fpa-D-Cys-Pal-D-Trp-Lys-Tle-Cys-Nal-NH$_2$ | (SEQ ID NO: 8) | 100 |
| Cpa-D-Cys-Tyr-D-Trp-Lys-Thr-Cys-Nal-NH$_2$ | (SEQ ID NO: 9) | 12 |
| Cpa-D-Cys-Pal-D-Trp-Lys-Tle-Cys-Nal-NH$_2$ | (SEQ ID NO: 10) | 10 |
| Cpa-D-Cys-Pal-Trp-Lys-Thr-Cys-Cpa-NH$_2$ | (SEQ ID NO: 11) | 2 |

Equivalents

Although the present invention has been described with reference to preferred embodiments, one skilled in the art can easily ascertain its essential characteristics and without departing from the spirit and scope thereof, can make various changes and modifications of the invention to adapt it to various usages and conditions. Those skilled in the art will recognize or be able to ascertain using no more than routine experimentation, many equivalents to the specific embodiments of the invention described herein. Such equivalents are intended to be encompassed in the scope of the present invention.

All publications and patents mentioned in this specification are herein incorporated by reference.

What is claimed is:

1. A urotensin-II polypeptide antagonist having the formula:

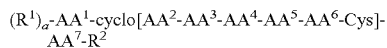

wherein
- AA$^1$ is the L isomer of an aromatic amino acid;
- AA$^2$ is the L or D isomer of Cys;
- AA$^3$ is an L isomer of an aromatic amino acid;
- AA$^4$ is L-Trp;
- AA$^5$ is the L or D isomer of Lys or Orn;
- AA$^6$ is the L or D isomer of Val, Thr, Leu, Ile, tert-Leu, Abu, Nle, or an aromatic amino acid;
- AA$^7$ is the L or D isomer of Val, Thr, Leu, Ile, tert-Leu, Abu, Nle, or an aromatic amino acid;
- R$^1$ is H, (C$_2$-C$_6$)lower alkyl, lower alkanoyl, or a lower acyl; a is 2; and R$^2$ is OH, OR$^3$, N(R$^3$)$_2$ or NHR$^3$, where R$^3$ is H, a lower alkyl, or arylalkyl;

or a pharmaceutically acceptable salt of said polypeptide.

2. A urotensin-II polypeptide antagonist having the formula:

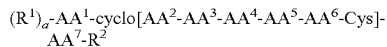

wherein
- AA$^2$ is D-Cys;
- AA$^3$ is Phe;
- AA$^4$ is Trp;
- AA$^5$ is Lys;
- AA$^6$ is Thr;
- AA$^7$ is Val;
- AA$^1$ is Cpa;
- R$^1$ is H, (C$_2$-C$_6$)lower alkyl, lower alkanoyl, or a lower acyl; a is 2; and R$^2$ is OH, OR$^3$, N(R$^3$)$_2$ or NHR$^3$, where R$^3$ is H, a lower alkyl, or arylalkyl;

or a pharmaceutically acceptable salt of said polypeptide.

3. A polypeptide having the formula Cpa-c[D-Cys-Phe-Trp-Lys-Thr-Cys]-Val-NH$_2$ (SEQ ID NO: 5).

4. A pharmaceutical composition comprising a polypeptide, and a pharmaceutically acceptable carrier, said polypeptide having the formula:

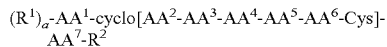

wherein
- AA$^1$ is the L isomer of an aromatic amino acid;
- AA$^2$ is the L or D isomer of Cys;
- AA$^3$ is an L isomer of an aromatic amino acid;
- AM$^4$ is L-Trp;
- AA$^5$ is the L or D isomer of Lys or Orn;
- AA$^6$ is the L or D isomer of Val, Thr, Leu, Ile, tert-Leu, Abu, Nle, or an aromatic amino acid;
- AA$^7$ is the L or D isomer of Val, Thr, Leu, Ile, tert-Leu, Abu, Nle, or an aromatic amino acid;
- R$^1$ is H, (C$_2$-C$_6$)lower alkyl, lower alkanoyl, or a lower acyl; a is 2; and R$^2$ is OH, OR$^3$, N(R$^3$)$_2$ or NHR$^3$, where R$^3$ is H, a lower alkyl, or arylalkyl;

or a pharmaceutically acceptable salt of said polypeptide.

5. A pharmaceutical composition comprising a polypeptide, and a pharmaceutically acceptable carrier, said polypeptide having the formula:

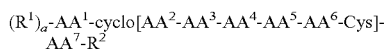

wherein
- AA is D-Cys;
- AA$^3$ is Phe;
- AA$^4$ is Trp;
- AA$^5$ is Lys;
- AA$^6$ is Thr;
- AA$^7$ is Val;
- AA$^1$ is Cpa;
- R$^i$ is H, (C$_2$-C$_6$)lower alkyl, lower alkanoyl, or a lower acyl; a is 2; and R$^2$ is OH, OR$^3$, N(R$^3$)$_2$ or NHR$^3$, where R$^3$ is H, a lower alkyl, or arylalkyl;

or a pharmaceutically acceptable salt of said polypeptide.

6. A pharmaceutical composition comprising a polypeptide having the formula Cpa-c[D-Cys-Phe-Trp-Lys-Thr-Cys]-Val-NH$_2$ (SEQ ID NO: 5) and a pharmaceutically acceptable carrier.

7. The pharmaceutical composition of claim 4, wherein said carrier is selected from the group consisting of saline, buffered saline, dextrose, water, glycerol, ethanol, and combinations thereof.

8. A method of preventing or treating an abnormal condition characterized by an excess of urotensin-II activity, said method comprising administering to a subject a therapeutically effective amount of a polypeptide according to claim 1 or a pharmaceutically acceptable salt thereof.

9. The method of claim 8, wherein said condition is selected from the group consisting of ischaemic heart disease, congestive heart failure, portal hypertension, variceal bleeding, hypotension, angina pectoris, myocardial infarction, ulcers, anxiety, schizophrenia, manic depression, delirium, dementia, mental retardation, and dyskinesias.

10. The method of claim 9, wherein said condition is ischaemic heart disease.

11. The method of claim 9, wherein said condition is congestive heart failure.

12. The method of claim 9, wherein said condition is portal hypertension.

13. The method of claim 9, wherein said condition is variceal bleeding.

14. A method of modulating the effect of urotensin-II, said method comprising administering to a subject a polypeptide according to claim 1 or a pharmaceutically acceptable salt thereof.

* * * * *